United States Patent
Kadobayashi et al.

(10) Patent No.: US 9,925,124 B2
(45) Date of Patent: Mar. 27, 2018

(54) DENTAL COMPOSITION SUITABLE FOR GRINDING WITH AUTOMATIC GRINDING APPARATUS

(75) Inventors: Yusei Kadobayashi, Kyoto (JP); Masako Shigezawa, Kyoto (JP); Keiji Takahashi, Kyoto (JP)

(73) Assignee: KABUSHIKI KAISHA SHOFU, Kyoto (JP)

(*) Notice: Subject to any disclaimer, the term of this patent is extended or adjusted under 35 U.S.C. 154(b) by 0 days.

(21) Appl. No.: 13/408,050

(22) Filed: Feb. 29, 2012

(65) Prior Publication Data
US 2013/0190422 A1    Jul. 25, 2013

(30) Foreign Application Priority Data
Jan. 24, 2012    (JP) .................. 2012-012223

(51) Int. Cl.
A61K 6/083    (2006.01)
A61K 6/00    (2006.01)
A61C 13/00    (2006.01)

(52) U.S. Cl.
CPC ........ A61K 6/0008 (2013.01); A61C 13/0022 (2013.01)

(58) Field of Classification Search
CPC .................................................. A61K 6/0008
USPC .................... 523/113, 115, 116, 117
See application file for complete search history.

(56) References Cited

U.S. PATENT DOCUMENTS

| | | | |
|---|---|---|---|
| 4,459,193 A * | 7/1984 | Ratcliffe et al. ................ 522/24 |
| 4,674,980 A | 6/1987 | Ibsen et al. | |
| 4,962,151 A * | 10/1990 | Mellon .......................... 524/788 |
| 5,116,885 A * | 5/1992 | Hattori et al. ................ 523/200 |
| 2002/0128347 A1 | 9/2002 | Blackwell et al. | |
| 2008/0319380 A1 | 12/2008 | Prabhu et al. | |
| 2010/0226820 A1* | 9/2010 | Prabhu et al. .................. 422/22 |
| 2013/0030080 A1* | 1/2013 | Kadobayashi et al. ....... 523/115 |

FOREIGN PATENT DOCUMENTS

| | | |
|---|---|---|
| EP | 0 273 657 | 7/1988 |
| GB | 1 544 776 | 4/1979 |
| JP | 2002-249373 | 9/2002 |

OTHER PUBLICATIONS

Japanese Office Action dated Apr. 24, 2012 in Japanese Patent Application No. 2012-012223.
USPTO Office Action dated Jun. 13, 2014 in related U.S. Appl. No. 13/218,779.

(Continued)

*Primary Examiner* — Michael Pepitone
(74) *Attorney, Agent, or Firm* — Wenderoth, Lind & Ponack, L.L.P.

(57) ABSTRACT

Provided is a dental composition comprising a first largest group of particles and resin matrix, wherein the first largest group consists of particles whose particle size ranges from 0.7 to 1.5 times the representative particle size of the first largest fraction in a population of particles included in the composition whose particle size ranges from 110 to 1000 μm; and wherein the ratio of the number of particles included in the first largest group to the number of particles whose particle size ranges from 0.5 to 2.0 times the representative particle size of the first largest fraction is equal to or more than 0.8.

10 Claims, 1 Drawing Sheet

(56) References Cited

OTHER PUBLICATIONS

USPTO Office Action dated Nov. 20, 2014 in related U.S. Appl. No. 13/218,779.
Extended European Search Report dated Jan. 9, 2015 in corresponding European Patent Application No. 12178522.4.
USPTO Office Action dated Jul. 14, 2015 in related U.S. Appl. No. 13/218,779.
R.K. McGeary, "Mechanical Packing of Spherical Particles", Journal of the American Ceramic Society, vol. 44, No. 10, pp. 514-522, 1961.

* cited by examiner

[Fig. 1]
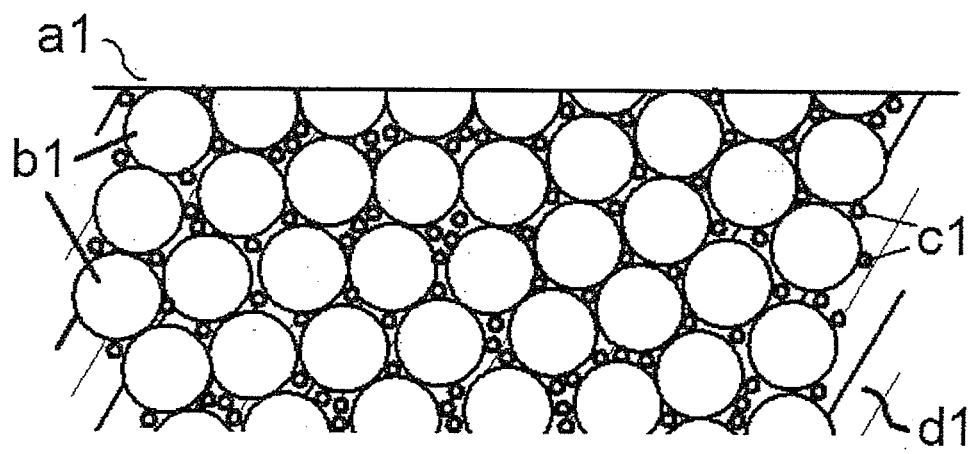
[Fig. 2]
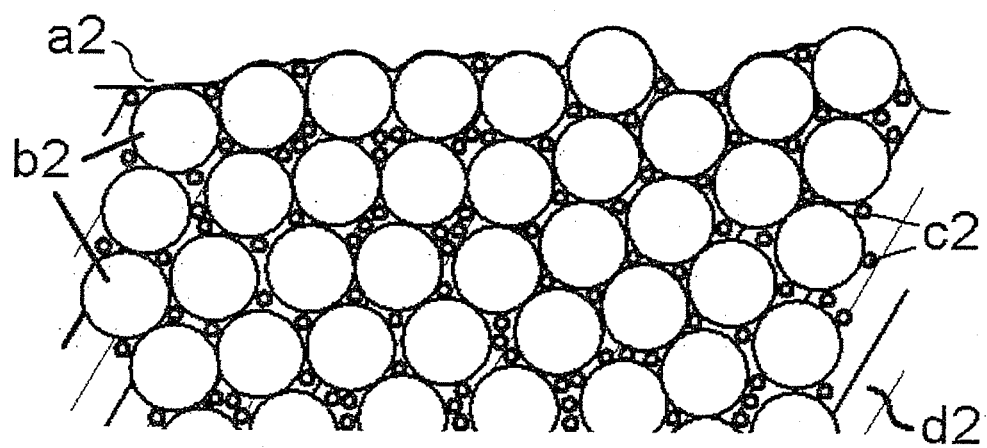

DENTAL COMPOSITION SUITABLE FOR GRINDING WITH AUTOMATIC GRINDING APPARATUS

FIELD OF THE INVENTION

The present invention relates to a dental composition. The present invention also relates to a dental block or a dental prosthesis that is made of the dental composition.

BACKGROUND ART

Dental compositions comprising filler and resin matrix are used as dental materials for repairing a portion missing from a tooth or for forming dental prostheses including artificial teeth. The dental compositions are provided in the form of paste. The dental composition changes from paste to hardened product by curing the resin matrix comprised in the dental compositions. Dental compositions when in the form of paste are desired to have an appropriate filling property that allows the paste being easily filled into a cavity of tooth, and a good preservation stability. The cured products formed from the dental compositions are desired to have a good mechanical strength, smooth surface, and adequate color tone comparable with natural teeth. In addition, cured dental products preferably provide cutting and grinding sensation comparable with that of natural teeth.

Dental compositions tend to shrink in association with polymerizing and curing the resin matrix. The degree of volumetric shrinkage is called a rate of polymerization shrinkage. When a dental composition with a high rate of polymerization shrinkage is filled to a missing part of a tooth and cured there, strain and gap may occur at the interface between the tooth and the dental composition, resulting in a poor adhesiveness and edge sealing. When such dental compositions as above are used as a filling material to fill a large cavity of tooth, there is a tendency for secondary caries to occur therein. Conventional dental compositions are insufficient in mechanical strength, e.g., bending strength and abrasion resistance when they are in the form of cured product.

When the dental compositions with a high rate of polymerization shrinkage are cured outside the oral cavity to from a dental block or a dental prosthesis, they have a strong propensity to develop high internal stress and cracks on the inside, resulting in the poor mechanical strength. When dental blocks are cut and ground to form a dental prosthesis, it is difficult to form an accurate dental prosthesis because the shape of the delicate or thin parts of the prosthesis tend to change.

Conventional dental materials had comprised relatively large size quartz particles as filler. Dental materials containing such large size filler possessed practically acceptable degree of shrinkage of the material upon polymerization of the material in the form of paste. The mechanical strength was also practically acceptable. However, the cured materials could provide only unsatisfying grinding and polishing feelings.

Dental materials containing ultrafine silica particles having particle size from 0.01 to 0.05 µm were developed. The dental material can provide a grinding sensation similar to that of natural teeth and can easily provide a smooth surface. However, the amount of the ultrafine particle filler in the dental material is limited due to high viscosity of the material containing a high amount of the filler when it is in the form of paste. Therefore, a cured product obtained from the paste of the dental material had unfavorable mechanical strength and abrasion resistance. In addition, degree of shrinkage of the material upon polymerization was also unfavorable. Hybrid-type dental materials having advantages of both aforementioned dental materials had been developed (JP-A 63-88110).

RELATED PRIOR ART

[Patent Literature 1] JP-A 63-88110

Conventional dental materials had been developed on the premise that dental technicians grind the cured material by hand with a dental router. Under the situation, the particle size of the fillers in the dental materials have decreased from about 150 µm to submicron. However, the dental compositions containing submicron filler particles exhibited unpractical rate of polymerization shrinkage.

When dental blocks are manufactured, cured products that are larger in size than those for manufacturing conventional dental prosthesis are formed. In the larger cured products, internal stress caused by polymerization shrinkage of the dental composition tends to increase. The increased internal stress reduces physical properties such as mechanical strength of the cured product.

There has been needs for dental compositions with a good filling property that makes it easier for dentists or dental technicians to handle it and those with a low rate of polymerization shrinkage as a filling material to fill a large cavity of tooth in the oral cavity. In addition, dental compositions with a good filling property that makes it easier for dentists and dental technicians to handle it and a good preservation stability when it is in the form of paste, as well as an excellent mechanical strength when it is in the form of cured product have been desired.

SUMMARY OF THE INVENTION

An object of the present invention is to provide a dental composition with an excellent filling property and preservation stability when it is in the form of paste and low rate of polymerization shrinkage that causes fewer sink marks when it is cured.

The first aspect of the present invention provides a dental composition comprising particles and resin matrix, wherein the particles comprises a first largest group of particles; wherein the first largest group consists of particles whose particle size ranges from 0.7 to 1.5 times the representative particle size of the first largest fraction in a population of particles included in the composition whose particle size ranges from 110 to 1000 µm; and wherein the ratio of the number of particles included in the first largest group to the number of particles whose particle size ranges from 0.5 to 2.0 times the representative particle size of the first largest fraction (=[the number of particles included in the first largest group]/[the number of particles whose particle size ranges from 0.5 to 2.0 times the representative particle size of the first largest fraction]) is equal to or more than 0.8.

In the first aspect of the present invention, the representative particle size of the first largest fraction in a population of particles ranges from more than 250 µm to 1000 µm or less, and preferably from 300 µm to less than 700 µm.

The second aspect of the present invention provides a dental composition comprising particles and resin matrix, wherein the particles comprises a first largest group of particles and a second largest group of particles, wherein the first largest group consists of particles whose particle size ranges from 0.7 to 1.5 times the representative particle size of the first largest fraction in a population of particles included in the composition whose particle size ranges from 10 to 1000 μm, provided that when the representative particle size of the first largest fraction is equal to or more than 110 μm, the ratio of the number of particles included in the first largest group to the number of particles whose particle size ranges from 0.5 to 2.0 times the representative particle size of the first largest fraction (=[the number of particles included in the first largest group]/[the number of particles whose particle size ranges from 0.5 to 2.0 times the representative particle size of the first largest fraction]) is equal to or more than 0.8, and when the representative particle size of the first largest fraction is less than 110 μm, the ratio of the number of particles included in the first largest group to the number of particles whose particle size ranges from 0.5 to 2.0 times the representative particle size of the first largest fraction is equal to or more than 0.6; and wherein the second largest group consists of particles whose particle size ranges from 0.7 to 1.5 times the representative particle size of the second largest fraction in a population of particles included in the composition whose particle size ranges from 10 to 1000 μm but excluding particles whose particle size ranges from 0.7 to 1.5 times the representative particle size of the first largest fraction, provided that when the representative particle size of the second largest fraction is equal to or more than 110 μm, the ratio of the number of particles included in the second largest group to the number of particles whose particle size ranges from 0.5 to 2.0 times the representative particle size of the second largest fraction (=[the number of particles included in the second largest group]/[the number of particles whose particle size ranges from 0.5 to 2.0 times the representative particle size of the second largest fraction]) is equal to or more than 0.8, and when the representative particle size of the second largest fraction is less than 110 μm, the number of particles included in the second largest group to the number of particles whose particle size ranges from 0.7 to 1.5 times the representative particle size of the second largest fraction is equal to or more than 0.6; and wherein the ratio of the representative particle size of the first largest fraction to the representative particle size of the second largest fraction (=[the representative particle size of the first largest fraction]/[the representative particle size of the second largest fraction]) is between 0.1 and 0.3, and the ratio of the number of particles in the first largest group to the number of particles in the second largest group ([the number of particles in the first largest group]/[the number of particles in the second largest group]) is between 0.7 and 4.0.

In the second aspect of the present invention, the representative particle size of the first largest fraction in a population of particles preferably ranges from 10 μm to 300 μm, and the representative particle size of the second largest fraction in a population of particles preferably ranges from 110 μm to 1000 μm.

The third aspect of the present invention provides a dental composition, obtainable by a process comprising a step of kneading a first largest group of particles and resin matrix, wherein the first largest group consists of particles whose particle size ranges from 0.7 to 1.5 times the representative particle size of the first largest fraction in a population of particles included in the composition whose particle size ranges from 110 to 1000 μm;

wherein the ratio of the number of particles included in the first largest group to the number of particles whose particle size ranges from 0.5 to 2.0 times the representative particle size of the first largest fraction (=[the number of particles included in the first largest group]/[the number of particles whose particle size ranges from 0.5 to 2.0 times the representative particle size of the first largest fraction]) is equal to or more than 0.8.

The fourth aspect of the present invention provides a dental composition, obtainable by a process comprising a step of kneading a first largest group of particles, a second largest group of particles, and resin matrix, wherein the first largest group consists of particles whose particle size ranges from 0.7 to 1.5 times the representative particle size of the first largest fraction in a population of particles included in the composition whose particle size ranges from 10 to 1000 μm, and the second largest group consists of particles whose particle size ranges from 0.7 to 1.5 times the representative particle size of the second largest fraction in a population of particles included in the composition whose particle size ranges from 10 to 1000 μm but excluding particles whose particle size ranges from 0.7 to 1.5 times the representative particle size of the first largest fraction, provided that when the representative particle size of the first largest fraction is equal to or more than 110 μm, the ratio of the number of particles included in the first largest group to the number of particles whose particle size ranges from 0.5 to 2.0 times the representative particle size of the first largest fraction (=[the number of particles included in the first largest group]/[the number of particles whose particle size ranges from 0.5 to 2.0 times the representative particle size of the first largest fraction]) is equal to or more than 0.8, and when the representative particle size of the first largest fraction is less than 110 μm, the ratio of the number of particles included in the first largest group to the number of particles whose particle size ranges from 0.5 to 2.0 times the representative particle size of the first largest fraction is equal to or more than 0.6; and when the representative particle size of the second largest fraction is equal to or more than 110 μm, the ratio of the number of particles included in the second largest group to the number of particles whose particle size ranges from 0.5 to 2.0 times the representative particle size of the second largest fraction (=[the number of particles included in the second largest group]/[the number of particles whose particle size ranges from 0.5 to 2.0 times the representative particle size of the second largest fraction]) is equal to or more than 0.8, and when the representative particle size of the second largest fraction is less than 110 μm, the ratio of the number of particles included in the second largest group to the number of particles whose particle size ranges from 0.7 to 1.5 times the representative particle size of the second largest fraction is equal to or more than 0.6; and wherein the ratio of the representative particle size of the first largest fraction to the representative particle size of the second largest fraction (=[the representative particle size of the first largest fraction]/[the representative particle size of the second largest fraction]) is between 0.1 and 0.3, and the ratio of the number of particles in the first largest group to the number of particles in the second largest group (=[the number of particles in the first largest group]/[the number of particles in the second largest group]) is between 0.7 and 4.0.

The present invention provides a cured material whose degree of shrinkage and sink marks are small. A cured material obtainable by curing the dental composition of the present invention is suitable for forming a dental prosthesis. In addition, a dental block obtainable by curing the dental composition of the present invention is suitable to be ground with an automatic program-controlled grinding machine. The dental composition of the present invention provides a paste whose stability during a storage and filling property are excellent.

BRIEF DESCRIPTION OF THE DRAWINGS

FIG. 1 shows a schematic of a cross-section of a dental composition of the present invention after curing. The "a1" represents a cross-section of a cured product, the surface of which was ground with a CAD/CAM system equipped with a dental router. The "b1" represents a particle included in a second largest group of particles in the cured product. The "c1" represents a particle included in a first largest group of particles in the cured product. The "d1" represents resin matrix of the cured product.

FIG. 2 shows a schematic of a cross-section of a dental composition of the present invention after curing. The "a2" represents a cross-section of a cured product, the surface of which was ground by hand of a dental technician using a dental router. The "b2" represents a particle included in a second largest group of particles in the cured product. The "c2" represents a particle included in a first largest group of particles in the cured product. The "d2" represents resin matrix of the cured product.

DETAILED DESCRIPTION OF THE INVENTION

In the present application, the term "dental composition" means a composition which can be used in dental field. The dental composition of the present invention comprises at least one kind of filler and resin matrix.

In the present application, the term "particles" means particles which are used as filer in dental compositions. The material of the particles may be inorganic material, organic material, or organic-inorganic composite material.

In the present invention, the materials of inorganic particles may be any inorganic material without any limitation that are generally used in dental compositions. Examples of inorganic materials include quartz, amorphous silica, aluminum silicate, aluminum oxide, titanium oxide, zirconium oxide, various glasses (including a glass made by a melting process and a synthesized glass made by a sol-gel process, etc), calcium carbonate, talc, kaolin, clay, mica, aluminum sulfate, calcium sulfate, barium sulfate, calcium phosphate, hydroxyapatite, silicon nitride, aluminum nitride, titanium nitride, silica carbide, boron carbide, calcium hydroxide, strontium hydroxide, and zeolite. Preferred are glasses such as aluminosilicate glass, borosilicate glass, aluminoborate glass, boroaluminosilicate glass containing sodium, fluorine, and/or heavy metal such as strontium, barium, or lanthanum. These inorganic materials may be used alone or in combination of two or more thereof.

The inorganic filler particles may be cohesive inorganic filler which is obtained by cohering ultrafine inorganic particles such as Aerosil particles prepared by a gas-phase process and silica-zirconia oxide particles prepared by a sol-gel process in a solution. In the present invention, these inorganic filler particles may be used alone or in combination of two or more thereof.

In an embodiment, the material of inorganic particles as filler is preferably glass. More preferably, the material of the inorganic particles is amino-silicate glass. Even more preferably, the chemical composition of the glass is from 60 to 90% by weight of $SiO_2$, from 5 to 20% by weight of $Al_2O_3$, and from 3 to 20% by weight of the other inorganic oxides based on the total weight of the glass composition. Examples of the other inorganic oxides include alkali metal oxide and coloring pigments. In the present invention, the glass may comprise at least one kind of alkali metal oxide selected from the group consisting of lithium oxide, beryllium oxide, sodium oxide, magnesium oxide; potassium oxide, calcium oxide, rubidium oxide, strontium oxide, cesium oxide, and barium oxide.

In the present invention, the materials of particles as filler may be a known organic resin that is available as dental material. Examples of the organic resin include, but are not limited to, (meth)acrylate-based resin. In the present application, the term "(meth)acrylate" or "(meth)acryloyl" represents inclusively both acryloyl group-containing polymerizable monomers and methacryloyl group-containing polymerizable monomers.

In the present invention, the organic materials of particles as filler may be monofunctional monomers (non-crosslinkable monomers) including (meth)acrylic acid esters such as methyl (meth)acrylate, ethyl (meth)acrylate, butyl (meth)acrylate, hexyl (meth)acrylate, tetrahydrofurfuryl (meth)acrylate, 2-hydroxyethyl(meth)acrylate, grycidyl (meth)acrylate, lauryl (meth)acrylate, cyclohexyl (meth)acrylate, benzil (meth)acrylate, allyl (meth)acrylate, 2-ethoxyethyl (meth)acrylate, methoxy polyethylene glycol (meth)acrylate, glycerol (meth)acrylate and isobornyl (meth)acrylate; silane compounds such as γ-(meth)acryloyloxypropyltrimethoxysilane and γ-(meth)acryloyloxypropyltriethoxysilane; nitrogen-containing compounds such as 2-(N,N-dimethylamino)ethyl (meth)acrylate, N-methylol (meth)acrylamide and diacetone (meth)acrylamide, aromatic bifunctional monomers (crosslkable monomers) such as 2,2-bis(4-(meth)acryloyloxyphenyl)propane, 2,2-bis(4-(3-(meth)acryloyloxy-2-hydroxypropoxy)phenyl) propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentathoxyphenyl)propane, 2,2-bis(4-(meth)acryloyloxydipropooxyphenyl)propane, 2,2-bis(4-(meth)acryloyloxyethoxyphenyl)-2-(4-(meth)acryloyloxydiethoyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl) propane, 2,2-bis(4-(meth)acryloyloxydipropoxyphenyl)propane and 2,2-bis(4-(meth)acryloyloxyisopropoxyphenyl)propane, aliphatic bifunctional monomers (crosslinkable monomers) such as 2-hydroxy-3-acryloyloxypropylmethacrylate, hydroxypivalic acid neopentylglycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butane diol di(meth)acrylate, 1,4-butanediol di(meth)acrylate, 1,6-hexanediol di(meth)acrylate and glycerin di(meth)acrylate, trifunctional monomers (crosslinkable monomers) such as trimethylolpropane tri(meth)acrylate, treimethylolethane tri (meth)acrylate, trimethylolmethane tri(meth)acrylate and pentaerythritol tri(meth)acrylate, tetrafunctional monomers (crosslinkable monomers) such as pentaerythritol tetra(meth)acrylate and ditrimethylolporpane tetra(meth) acrylate.

In the present invention, the materials of particles as filler may be a known organic-inorganic composite material that can be used as dental material. The organic-inorganic composite may be particles which are obtainable by mixing inorganic particles and polymerizable monomers, polymerizing the mixture and then pulverizing the polymerized mixture. In the organic-inorganic composite material, the inorganic particles are dispersed in the polymer matrix. The inorganic particles constituting the organic-inorganic composite material may be any of the aforementioned inorganic particles that can be used as filler in the dental composition of the present invention. Examples of the inorganic particles may be, without any limitation, colloidal silica (e.g., trade name: Aerosil R972, Aerosil 200, Aerosil 380, Aerosil 50 (Nippon Aerosil Co., Ltd.)). In addition, the polymer matrix constituting the organic-inorganic composite material may be any of the aforementioned organic materials that are used in the dental composition of the present invention as organic materials.

In an embodiment of the first aspect of the present invention, at least one kind of filler in a dental composition of the present invention comprises a first largest group consisting of particles whose particle size ranges from 0.7 to 1.5 times the representative particle size of the first largest fraction in a population of particles included in the composition whose particle size ranges from 110 to 1000 μm. The ratio of the number of particles included in the first largest group to the number of particles whose particle size ranges from 0.5 to 2.0 times the representative particle size of the first largest fraction is equal to or more than 0.8, preferably equal to or more than 0.85, and more preferably equal to or more than 0.9; and wherein the amount of the at least one kind of fillers in the composition is from 65.0 to 99.5% by weight based on the total weight of the dental composition.

In an embodiment of the second aspect of the present invention, at least one kind of filler in a dental composition of the present invention comprises a first largest group of particles and a second largest group of particles. The first largest group consists of particles whose particle size ranges from 0.7 to 1.5 times the representative particle size of the first largest fraction in a population of particles included in the composition whose particle size ranges from 10 to 1000 μm. When the representative particle size of the first largest fraction is equal to or more than 110 μm, the ratio of the number of particles included in the first largest group to the number of particles whose particle size ranges from 0.5 to 2.0 times the representative particle size of the first largest fraction is equal to or more than 0.8, preferably equal to or more than 0.85, and more preferably equal to or more than 0.9. When the representative particle size of the first largest fraction is less than 110 μm, the ratio of the number of particles included in the first largest group to the number of particles whose particle size ranges from 0.5 to 2.0 times the representative particle size of the first largest fraction is equal to or more than 0.6, preferably equal to or more than 0.65, and more preferably equal to or more than 0.7.

The second largest group consists of particles whose particle size ranges from 0.7 to 1.5 times the representative particle size of the second largest fraction in a population of particles included in the composition whose particle size ranges from 10 to 1000 μm but excluding particles whose particle size ranges from 0.7 to 1.5 times the representative particle size of the first largest fraction. When the representative particle size of the second largest fraction is equal to or more than 110 μm, the ratio of the number of particles included in the second largest group to the number of particles whose particle size ranges from 0.5 to 2.0 times the representative particle size of the second largest fraction is equal to or more than 0.8, preferably equal to or more than 0.85, and more preferably equal to or more than 0.9. When the representative particle size of the second largest fraction is less than 110 μm, the number of particles included in the second largest group to the number of particles whose particle size ranges from 0.5 to 2.0 times the representative particle size of the second largest fraction is equal to or more than 0.6, preferably equal to or more than 0.65, and more preferably equal to or more than 0.7.

The ratio of the representative particle size of the first largest fraction to the representative particle size of the second largest fraction is between 0.1 and 0.3, between 0.15 and 0.27, or between 0.2 and 0.24, and the ratio of the number of particles in the first largest group to the number of particles in the second largest group is between 0.7 and 4.0, between 0.7 and 3.0, between 0.7 and 2.0, or between 0.7 and 1.5. The amount of the at least one kind of fillers comprising the first largest group of particles and the second largest group of particles in the composition is from 65.0 to 99.5% by weight based on the total weight of the dental composition.

In an embodiment of the second aspect of the present invention, the filler comprised in the dental composition of the present invention consists of a first largest group of particles and a second largest group of particles.

In the present invention, the amount of the at least one kind of filler is from 65.0 to 99.5%, preferably from 70 to 98%, and more preferably from 80 to 95% by weight based on the total weight of the dental composition.

In another embodiment of the second aspect of the present invention, a dental composition further comprises ultrafine particles whose particle size is less than 1 μm and the average particle size is from 1 nm to 300 nm. The ultrafine particles may be, without any limitation, colloidal silica (trade names: Aerosil R972, Aerosil 200, Aerosil 380, Aerosil 50 (Nippon Aerosil Co., Ltd.)). The average particle size of the ultrafine particles is about 16 nm (Aerosil R972), 12 nm (Aerosil 200), 7 nm (Aerosil 380), and 30 nm (Aerosil 50), respectively. In an embodiment of this aspect, the amount of the ultrafine particle is from 0.1 to 5.0% by weight based on 100% weight of the dental composition comprising a first largest group of particles, a second largest group of group, an ultrafine particle, and resin matrix.

In the present application, "particle size" is obtained by imaging the particles with a microscope and measuring unidirectional particle diameters (Green diameters) of the particles on the image. For example, the size of particles in a dental composition comprising the particles as filler and resin matrix may be measured after isolating the fillers from the composition. When the dental composition is in the form of paste, the fillers may be isolated by dissolving the resin matrix with a solvent such as, e.g. acetone. When the dental composition is in the form of cured product, the filler included in the cured product may be isolated by heating the cured product at about 400° C. to melt the resin matrix. In the present application, "average particle size" refers to an arithmetic mean of particle sizes obtained from data of plural particles. An average particle size may be calculated, without any limitation, from particle sizes of a thousand particles in a sample measured as described above.

In the present application, "the first largest fraction in a population of particles" means the class with the highest frequency in a frequency distribution table for the size of the particles whose particle size ranges from 0.5 to 2.0 times the representative particle size of a class with the highest frequency in a frequency distribution table which is previously constructed for particles which exist in a predetermined range of particle size. "The representative particle size of a class" means the average of the largest and smallest particles in the class (i.e. class value). In the present application, the predetermined range of particle size is from 110 µm to 1000 µm, or from 10 µm to 1000 µm.

A frequency distribution table can be, without any limitation, constructed as follows. Individual particles of the filler included in a dental composition or in a filler sample are measured and the total number (n) of the particles in the predetermined range of particle size is determined. The number of classes may be calculated from the total number (n) by means of, for example, square-root choice ($\sqrt{n}$) or Sturges' formula ($[\log_2 n+1]$). The number of classes is an integer, which may be any of the results calculated with the above equations, or any of integers between the calculated results. A range of particle size is the difference between the minimum and maximum sizes of the measured particles in the predetermined range. The range of particle size is divided by the number of classes to obtain the class width (w). The class width (w) may be processed to give an appropriate number by means of, for example, rounding off the divided result. The class width (w) may be, but is not limited to, 30 µm, 20 µm, 15 µm, 10 µm, 5 µm or 1 µm. The data of the particles in the predetermined range are split into the classes so as to construct a frequency distribution table. The frequency distribution table with regard to particle size is constructed with the particle size data of 500 to 2000 particles, e.g., 1000 particles included in a dental composition or a particle sample.

In the present application, "the first largest group of particles" means the group consisting of particles whose particle size ranges from 0.7 to 1.5 times the representative particle size of the first largest fraction in a population of particles.

In the present application, "the second largest group of particles" means the class with the highest frequency in a frequency distribution table for the size of particles whose particle size ranges from 0.5 to 2.0 times the representative particle size of a class with the highest frequency in a frequency distribution table which is previously constructed for particles whose particle size ranges from 10 µm to 1000 µm but excluding particles whose particle size ranges from 0.7 to 1.5 times the representative particle size of the first largest fraction. In the present application, "the representative particle size of the second largest fraction" means the representative particle size of the class which represents the second largest fraction in a population of particles.

In the present application, "the second largest group of particles" means the group consisting of particles whose particle size ranges from 0.7 to 1.5 times the representative particle size of the second largest fraction in a population of particles.

In the present invention, the filler particles may be commercially available raw particles that can be generally used as fillers for dental products. The particles having a desired particle size distribution may be obtained by pulverizing the raw particles. The pulverization may be performed by a wet or dry process which is commonly used in the dental field. Examples of the equipments for the pulverization may include a high-speed rotation mill such as a hammer mill and a turbo mill, a container-driven medium mill such as a ball mill and an oscillating mill, a grinding medium agitating mill such as a sand grinder and an attritor, and a jet mill. In order to obtain particles having a relatively-small average particle size, a wet-grinding procedure in an aqueous medium is preferable. As the aqueous medium, water may be used alone or in combination with alcohols, ethers, ketones and the like which are miscible with water. The conditions for the wet-grinding may vary depending upon the size hardness and amount of the particles to be processed as well as the type and amount of the aqueous medium to be added. The conditions or the equipment for grinding may be appropriately selected depending upon the desired average particle size of the particles.

In the present invention, preferably, the degree of circularity of particles in the dental composition ranges from 0.7 to 1.0, preferably from 0.9 to 1.0, and more preferably from 0.95 to 1.00.

In the present invention, the degrees of circularity of the particles are determined by taking image of the particles with a light microscope or a scanning electron microscope (SEM) and analyzing the image with an image analyzer. The number of particles to be analyzed per sample may be 50 or more. The degree of circularity of the particles $e=(4*\pi*S)/(L^2)$ is calculated with boundary lengths (L) and area (S) of the particles which are obtained by analyzing the image.

In the present invention, particles included in the dental composition preferably have refractive index ranging from 1.46 to 1.58 and more preferably from 1.49 to 1.54. The preferred difference in refractive index between the particles and the resin matrix of the dental composition is 0.03 or less and preferably 0.01 or less.

The resin matrix of the dental composition of the present invention comprises a polymerizable monomer and a polymerization initiator. The above polymerizable monomer may be, without any limitation, known monofunctional or multifunctional polymerizable monomers which are generally used for manufacturing dental compositions. The polymerizable monomers are preferably those having an acryloyl group and/or a methacryloyl group.

Examples of polymerizable monomers having no acidic group include, monofunctional monomers (non-crosslinkable monomers), e.g., (meth)acrylic acid esters such as methyl (meth)acrylate, ethyl (meth)acrylate, butyl (meth)acrylate, hexyl (meth)acrylate, tetrahydrofurfuryl (meth)acrylate, 2-hydroxyethyl (meth)acrylate, grycidyl (meth)acrylate, lauryl (meth)acrylate, cyclohexyl (meth)acrylate, benzil (meth)acrylate, allyl (meth)acrylate, 2-ethoxyethyl (meth)acrylate, methoxy polyethylene glycol (meth)acrylate, glycerol (meth)acrylate and isobornyl (meth)acrylate; silane compounds such as γ-(meth)acryloyloxypropyltrimethoxysilane and γ-(meth)acryloyloxypropyltriethoxysilane; nitrogen-containing compounds such as 2-(N,N-dimethylamino)ethyl (meth)acrylate, N-methylol (meth)acrylamide and diacetone (meth)acrylamide, aromatic bifunctional monomers (crosslinkable monomers), e.g., 2,2-bis(4-(meth)acryloyloxyphenyl)propane, 2,2-bis(4-(3-(meth)acryloyloxy-2-hydroxypropoxy)phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropooxyphenyl)propane, 2(4-(meth)acryloyloxyethoxyphenyl)-2-(4-(meth)acryloyloxydiethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)

acryloyloxydipropoxyphenyl)propane and 2,2-bis(4-(meth) acryloyloxyisopropoxyphenyl)propane, aliphatic bifunctional monomer (crosslinkable monomers), e.g., 2-hydroxy-3-acryloyloxypropylmethacrylate, hydroxypivalic acid neopentylglycol di(meth)acrylate, ethylene glycol di(meth)acrylate, diethylene glycol di(meth) acrylate, triethylene glycol di(meth)acrylate, butylene glycol di(meth)acrylate, polyethylene glycol di(meth)acrylate, neopentyl glycol di(meth)acrylate, propylene glycol di(meth) acrylate, 1,3-butanediol di(meth)acrylate, 1,4-butanediol (meth)acrylate, 1,6-hexanediol di(meth)acrylate, and glycerin di(meth)acrylate, trifunctional monomer (crosslinkable monomers), e.g., trimethylolpropane tri(meth)acrylate, treimethylolethane tri (meth)acrylate, trimethylolmethane tri(meth)acrylate and pentaerythritol tri(meth) acrylate, tetrafunctional monomer (crosslinkable monomers), e.g., pentaerythritol tetra(meth)acrylate and ditrimethylolporpane tetra (meth) acrylate.

Examples of urethane-based polymerizable monomers may include di(meth)acrylates having a bifunctional or trifunctional or more-functional urethane linkage which are derived from an adduct of a polymerizable monomer having a hydroxy group such as 2-hydroxyethyl (meth)acrylate, 2-hydroxypropyl (meth)acrylate and 3-chloro-2-hydroxypropyl (meth)acrylate, and a diisocyanate compound such methylcyclohexane diisocyanate, methylene bis(4-cyclohexyl isocyanate), isophorone diisocyanate, diisocyanate methylbenzene and 4,4-diphenylmethane diisocyanate.

In addition to the aforementioned (meth)acrylate-based polymerizable monomers, other polymerizable monomers, for example, a monomer, an oligomer or a polymer having at least one polymerizable group in the molecule may be used for resin matrix of the dental composition of the present invention if desired. The polymerizable monomers may have a substituent such as an acidic group and a fluoro group in the molecule. In the present invention, the resin matrix may comprise a single polymerizable or a mixture of a plurality of polymerizable monomers. In addition, when the viscosity of a polymerizable monomer is extremely high at room temperature or the polymerizable monomer is solid at room temperature, said monomer is preferably used with a polymerizable monomer having a low viscosity. The mixture may comprise two, three or more kinds of polymerizable monomers.

The resin matrix of the dental composition of the present invention may include only monofunctional polymerizable monomers, and may additionally include polyfunctional polymerizable monomers. A preferred resin matrix of the present invention may include an aromatic bifunctional polymerizable monomer and an aliphatic bifunctional polymerizable monomer. More preferably, the resin matrix of the present invention may includes 2,2-bis(4-(3-methacryloyloxy-2-hydroxypropoxy)phenyl)propane (Bis-GMA) and triethylene glycol dimethacrylate (TEGDMA).

In the present invention, the resin matrix may include polymerizable monomers containing an acid group such as phosphoric acid group, carboxylic acid group, phosphonic acid, sulfonic acid group or the like in the molecule as a part or the whole of the polymerizable monomers so that the dental composition of the present invention can adhere to the teeth substance and a nonprecious metal. In order to enhance the property to adhere a precious metal the resin matrix of the present invention may include a polymerizable monomer containing a sulfur atom in the molecule. The resin matrix may include carboxylilc acid group-containing polymerizable monomers, e.g., (meth)acrylic acid, 1,4-di(meth)acryloyloxyethyl-pyromellitic acid, 6-(meth)acryloyloxynaphtalene-1,2,6-tricarboxylic acid, N-(meth)acryroyl-p-aminobenzoic acid, N-(meth)acryroyl-5-aminosalicylic acid, 4-(meth)acryroyloxyethyltrimellic acid and anhydride thereof, 4-(meth)acryroyloxybutyltrimellic acid and anhydride thereof, 2-(meth)acryroyloxybenzoic acid, β-(meth) acryroyloxyethyl hydrogen succinate, β-(meth)acryroyloxyethyl hydrogen maleate, 11-(meth)acryloyloxy-1,1-undecanedicarboxylic acid and p-vinylbenzoic acid; phosphate group-containing monomers, e.g., 2-(meth)acryloyloxyethyl hydrogen phosphate, 3-(meth)acryloyloxypropyl dihydrogen phosphate, 10-(meth)acryloyloxydecyl hydrogen phosphate, bis(2-(meth)acryloyloxyethyl)dihydrogen phosphate and 2-(meth)acryloyloxyphenyl hydrogen phosphate; sulfonic group-containing monomers, e.g., 2-(meth)acrylamide-2-methylpropanesulfonic acid, 4-(meth)acryloyloxybenzenesulfonic acid and 3-(meth) acryloyloxypropanesulfonic acid; sulfur atom-containing monomers, e.g., (meth)acrylate having a triazinethiol group, (meth)acrylate having a mercapto group, (meth)acrylate having a polysulfide group, (meth)acrylate having a thiophosphate group, (meth)acrylate having a disulfide cyclic group, (meth)acrylate having a mercaptodithiazole group, (meth)acrylate having a thiouracil group and (meth)acrylate having a thiirane group.

These polymerizable monomers may be used alone or in mixture of two or more kinds.

In an embodiment, a known radical generator may be used as a polymerization initiator. Polymerization initiators are generally classified into chemical polymerization initiator that initiates polymerization by mixing the same with the monomers upon use, thermal polymerization initiator that initiates polymerization by heating or warming the composition, and photoinitiator that initiates polymerization by light irradiation.

In an embodiment, examples of chemical polymerization initiators may include redox type polymerization initiator systems comprising an organic peroxide/an amine compound or an organic peroxide/an amine compound/a sulfinic acid salt, or an organic peroxide/an amine compound/a borate compound, and organometal type initiator systems which initiate polymerization by reacting with oxygen or water. In the chemical polymerizable initiators, sulfinic acid salts and borate compounds can also initiate the polymerization by reacting with a polymerizable monomer having an acidic group.

Examples of the aforementioned organic peroxides may include benzoylperoxide, parachlorobenzoylperoxide, 2,4-dichlorobenzoyl peroxide, acetyl peroxide, lauroyl peroxide, tertiary-butyl peroxide, cumene hydroperoxide, 2,5-dihydroperoxy-2,5-dimethylhexane, methyl ethyl ketone peroxide, and tertiary-butyl peroxide benzoate. Examples of the aforementioned amine compounds may include a secondary or tertiary amine in which an amine group is bound to an aryl group, and particular examples thereof are p-N,N-dimethyltoluidine, N,N-dimethylaniline, N-β-hydroxyethylaniline, N,N-di(β-hydroxyethyl)aniline, p-N,N-di(β-hydroxyethyl) toruidine, N-methylaniline, and p-N-methyltoluidine. Examples of the aforementioned sulfuric acid salts may include sodium benzenesulfinate, lithium benzenesulfinate, and sodium p-toluenesulfinate. Examples of the aforementioned borate compounds include, but are not limited to, trialkylphenylboron, and a sodium salt, a lithium salt, a potassium salt, a magnesium salt, a tetrabutyl ammonium salt and a tetramethyl ammonium salt of trialkyl (p-fluorophenyl)boron (wherein the alkyl group is n-butyl group, n-octyl group, n-dodecyl group or the like). Examples of the aforementioned organometal type polymerizable initiators may include organic boron compounds such as triphenylborane, tributylborane, and a partial oxide of tributylborane.

In an embodiment, azo compounds such as azobisisobutyronitrile, methyl azobisisobutyrate and azobiscyano valeric acid may be used as a thermal polymerization initiator that initiates the polymerization by heating or warming the composition in addition to the aforementioned organic peroxide.

In an embodiment, the photoinitiator may be a photosensitizer. The photosensitizer may be used alone or in combination with a photopolymerization promotor. Examples of the aforementioned photosensitizers may include α-diketones such as benzil, camphorquinone, α-naphtil, acetonaphtone, p,p'-dimethoxybenzil, p,p'-dichlorobenzylacetyl, pentadione, 1,2-phenanthrenquinone, 1,4-phenanthrenquinone, 3,4-phenanthrenquinone, 9,10-phenanthrenquinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphineoxides such as 2,4,6-trimethylbenzoyl diphenylphosphineoxide and bis(2,6-dimethoxybenzoyl)-2,4,4-trimethylpentylphosphineoxide; α-aminoacetophenones such as 2-benzyl-dimethylamino-1-(4-morpholinophenyl)-butanone-1,2-benzyl-diethylamino-1-(4-morpholinophenyl) propanone-1; ketals such as benzyldimethylketal, benzyldiethylketal and benzyl(2-methoxyethylketal); titanocenes such as bis(cyclopentadienyl)-bis[2,6-difluoro-3-(1-pyrolyl) phenyl]titanium, bis(cyclopentadienyl)-bis(pentanefluorophenyl)titanium and bis(cyclopentadienyl)-bis(2,3,5,6-tetrafluoro-4-disiloxyphenyl)-titanium.

Examples of the aforementioned photopolymerization promotors may include tertiary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoicacid ethyl ester, p-demtethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopyridine, N,N-dimethyl-α-naphthylamie N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino) diethanol; secondary amines such as N-phenylglycine; barbituric acids such as 5-butylbarbituric acid and 1-benzyl-5-phenylbarbituric acid; tin compounds such as dibutyltin diacetate, dibutyltin dilaurate, dioctyltin dilaurate, dioctyltin diperacetate, dioctyltin bis(mercaptoacetic acid isooctyl ester) salt and tetramethyl-1,3-diacetoxydistannoxane; aldehyde compounds such as laurylaldehyde and terephthalaldehyde; sulfur-containing compounds such as dodecylmercaptan, 2-mercaptobenzooxazole, 1-decanethiol and thiosalicylic acid.

In an embodiment of the present invention, resin matrix of the dental composition comprising the aforementioned photopolymerizatin promoter may further include an oxycarboxylic acid such as citric acid, maleic acid, tartaric acid, glycolic acid, gluconic acid, α-oxyisobutyric acid, 2-hydroxypropioic acid, 3-hydroxybutanoic acid, 4-hydroxybutanoic acid, and dimethylolpropioic acid to improve the photopolymerization promoting ability.

In the present invention, those polymerization initiators may be used alone or as a mixture of two or more thereof. In addition, these polymerization initiators may be used in combination irrespective of the polymerization form and the kind of polymerization initiators. The amount of a polymerization initiator to be added may be appropriately determined depending upon the use. In general, the amount may be selected from a range of 0.1-10 parts by weight based on a polymerizable monomer.

In an embodiment, the polymerization initiator is a photopolymerization initiator. The dental composition which comprises a photopolymerization initiator is relatively easy to be polymerized without air bubble entrainment. In a preferred embodiment, the photopolymerization initiator is a combination of an α-diketone and a tertiary amine and more preferably, a combination of camphorquinone with an aromatic amine having an amino group directly bound to the benzene ring such as ethyl p-N,N-dimethylaminobenzoate or with an aliphatic amine having a double bond in the molecule such as N,N-dimethylaminoethyl methacrylate. In another embodiment, the dental composition of the present invention may comprise, depending upon the use, a sensitizing pigment such as coumalin, cyanine, and thiazine; a light acid generator which produces Broensted acid or Lewis acid by light irradiator such as a s-triazine derivative substituted with a halomethyl group or diphenyl iodonium salt compound; quaternary ammonium halides; and transition metal compound.

In an embodiment of the present invention, a resin of the dental composition may be colored with a coloring pigment. The coloring pigments are classified into inorganic pigments and organic pigments. Examples of inorganic pigments may include chromates such as chrome yellow, zinc yellow and barium yellow; ferrocyanides such as Prussian blue; sulfides such as vermilion, cadmium yellow, zinc sulfide, antimony white and cadmium red; sulfates such as barium sulfate, zinc sulfate and strontium sulfate; oxides such as zinc white, titanium white, blood red, black iron oxide and chromium oxide; hydroxides such as aluminum hydroxide; silicates such as calcium silicate and ultramarine; and carbons such as carbon block and graphite. Examples of organic pigments may include nitoroso pigments such as Naphthol Green B and Naphthol Green Y; nitoro pigments such as Naphthol S and Lithol Fast Yellow 2G; insoluble azo pigments such as Permanent Red 4R, Brilliant Fast Scarlet, Hanza Yellow and Benzidine Yellow; poorly-soluble azo pigments such as Lithol Red, Lake Red C and Lake Red D; soluble azo pigments such as Brilliant Caramine 6B, Permanent Red F5R, Pigment. Scarlet 3B and Bordeaux 10B; phthalocyanine pigments such as Phthalocyanine Blue, Phthalocyanine Green and Sky Blue; basic dye pigments such as Rhodamine Lake, Malachite Green Lake and Methyl Violet Lake; and acidic dye pigments such as Peacock Blue Lake, Eosin Lake and Quinoline Yellow Lake. These pigments may be used alone or in combination of two or more thereof. In an embodiment, the coloring pigment is preferably an inorganic pigment, preferably titanium white, blood red, black iron oxide or yellow iron oxide.

The particles used in the dental composition of the present invention may be, without any limitation, inorganic particles whose surface is covered with poly(organo)siloxane. Preferably, the particles may be silane-treated inorganic particles. More preferably, glass particles which are colored by mixing the silane-treated glass with a coloring pigment described above.

In the present invention, glass particles may be, without any limitation, colored by mixing the raw material glass with a coloring agent. Such coloring agents as above may include iron, manganese, copper, chromium, zirconium, cobalt, tin, titanium, nickel, and vanadium. Particular examples of the coloring agents may be iron oxide, red oxide, manganese dioxide, manganese carbonate, copper oxide, chromium oxide, zirconium silicate, cobalt oxide G, tin oxide, titanium oxide, iron silicate, nickel oxide, ammonium metavanadate, and boron oxide.

The degree of coloring of glass particles is preferably adjusted to the range of Lab shown below. The color of the glass particles may be adjusted by increasing or decreasing the amount of the coloring agents.

$L^*$=50 to 75, $a^*$=−4 to −1, $b^*$=−8 to 4.

In the present invention, the dental composition may be made by mixing glass particles as filler and the resin matrix. Mixing procedures may include, but are not limited to, simply mixing the glass particles with the resin matrix and the polymerization initiator.

The dental composition of the present invention may comprise an ultraviolet absorbing agent such as 2-hydroxy-4-methylbenzophenone; polymerization inhibitors such as a hydroquinone, a hydroquinone monomethyl ether and 2,5-di(tertiary-butyl)-4-methylphenol; an anti-discoloring agent; an antimicrobial agent; and the other conventional known additive. The dental composition of the present invention may be packed in a single package, or divided into two packs or the other type packages. The package of the composition may be determined depending upon the kind of polymerization initiator or the use.

The dental composition of the present invention may be used, without any limitation, as a composite material for repairing odontic defect, as well as a material for forming a dental block, a dental plate, a dental prosthesis, e.g., artificial tooth. The dental block is cut and ground to produce an artificial tooth, an inlay, and an onlay. The dental composition of the present invention may be used, without any limitation, as a repairing agent to repair a dental prosthesis, e.g., prosthetic tooth.

The present invention provides a dental block or a dental prosthesis formed from the dental composition of the present invention. In an embodiment of the present invention, a dental block is preferably in a form of column (e.g., cylinder or prism), cone (e.g., circular cone or polyhedral cone), or dental plate with a thickness ranging from 1.5 to 3 cm and a wide ranging from 7 to 12 cm.

A dental block formed from the dental composition of the present invention may be, without any limitation, processed by a mechanical grinding apparatus which is controlled by a program in an automatic manner. Preferably, the dental block according to the present invention is processed by a CAD/CAM system. A CAD/CAM system may comprise, without any limitation, means for obtaining geometrical data of the oral cavity of a patient, in silico means for designing a dental prosthesis such as a prosthetic tooth, and an automatic mechanical grinding apparatus for processing the dental block on the basis of the design to give the dental prosthesis.

In a preferred embodiment of the present invention, a resin block for dental plate which is formed from a dental composition comprising organic particles as filler and resin matrix whose main resin is the same as that of the organic particles. The term "main resin" means the resin included in the resin matrix or organic particles in an amount 50% or more, preferably 80% or more, more preferably 100% based on the total weight of the resin matrix or organic particles. When the component of the main resin of the resin matrix is the same as that of the main resin of the organic particles and the amount of the main resin in each is 50% or more based on the total weight of the resin matrix or organic particles, a cured product of a dental composition which comprises said resin matrix and organic particles can easily be ground by a dental router without unpleasant grinding sensation and provides less impact on the edge of the dental router. A cured product of a dental composition which comprises the resin matrix and the organic particles shearing a main resin in an amount more than 80% each is more preferred because interface between the organic particles and the resin matrix is hardly generated in the cured product.

In an embodiment of the present invention, the organic filler and resin matrix contain above described crosslinkable monomers. In this embodiment, the amount of the crosslinkable monomers may be ranging from 0.1 to 60%, preferably from 0.1 to 25% based on the total weight of the resin matrix. Organic fillers containing a cross-linking agent hardly expand and therefore, are preferable. Resin matrixes containing a cross-linking agent are preferable since the shape of the cured product comprising the resin matrix is hardly changed with heat caused by the cutting work.

In the present application, the term "dental prosthesis" includes, but is not limited to, an artificial tooth, a dental plate, an inlay, a clown, a bridge, and an artificial tooth.

The dental composition of the present invention is used, without any limitation, as a filling material for a cavity of tooth in the oral cavity. The dental composition of the present invention is preferably used as a material for an enamel portion, a dentin portion, or a base of an artificial tooth. Preferably, the dental composition of the present invention may be colored depending upon the portion such as enamel portion to be applied. In present invention, a prosthetic tooth may be made by anchoring an artificial tooth to a dental plate which is formed from the dental composition of the present invention.

EXAMPLES

Glass particles were prepared by melting and pulverizing glass, the compositions of which are shown in Table 1.

TABLE 1

| Component | Glass 1 (% by weight) | Glass 2 (% by weight) | Glass 3 (% by weight) | Glass 4 (% by weight) |
|---|---|---|---|---|
| $SiO_2$ | 67 | 70 | 69 | 72 |
| $Al_2O_3$ | 13 | 13 | 10 | 10 |
| $B_2O_3$ | 18 | 15 | 18 | 15 |
| $Na_2O$ | 2 | 2 | 3 | 3 |
| Refractive index | 1.5195 | 1.5304 | 1.5204 | 1.5359 |
| Vickers hardness (HV200) | 520 | 535 | 530 | 538 |

The prepared glass particles were dried, dispersed in a high temperature atmosphere and shaped to provide spherical particles. The glass shown as Glass 1 in Table 1 were used in the Examples. The degree of circularity of the particles used in the examples was 0.95 or more. With regard to the glass particles used in the Examples, the representative particle size of the first largest fraction, the number of particles included in a group of particles whose particle size ranges from 0.7 to 1.5 times the representative particle size of the first largest fraction (i.e., the number of particles included in "the first largest group"), the number of particles included in a group of particles whose particle size ranges from 0.5 to 2.0 times the representative particle size of a first largest fraction, and the ratio of the number of particles included in the first largest group to the number of particles whose particle size ranges from 0.5 to 2.0 times the representative particle size of the first largest fraction are shown in Tables 2 and 3.

TABLE 2

| Glass particles | Representative particle size of the first largest fraction [μm] | Number of particles included in the first largest group | Number of particles included in a group of particles whose particle size ranges from 0.5 to 2.0 times the representative particle size of a first largest fraction | Ratio of the number of particles included in the first largest group to the number of particles whose particle size ranges from 0.5 to 2.0 times the representative particle size of the first largest fraction |
| --- | --- | --- | --- | --- |
| A | 120 | 659 | 812 | 0.81 |
| B | 160 | 645 | 759 | 0.85 |
| C | 200 | 592 | 695 | 0.85 |
| D | 250 | 701 | 854 | 0.82 |
| E | 300 | 692 | 818 | 0.85 |
| F | 310 | 640 | 794 | 0.81 |
| G | 300 | 703 | 769 | 0.91 |
| H | 310 | 752 | 825 | 0.91 |
| I | 310 | 784 | 862 | 0.91 |
| J | 490 | 692 | 813 | 0.85 |
| K | 510 | 869 | 901 | 0.96 |
| L | 690 | 746 | 893 | 0.84 |
| M | 810 | 694 | 745 | 0.93 |
| N | 900 | 629 | 778 | 0.81 |
| O | 910 | 624 | 759 | 0.82 |

TABLE 3

| Glass particles | Representative particle size of the first largest fraction [μm] | Number of particles included in the first largest group | Number of particles included in a group of particles whose particle size ranges from 0.5 to 2.0 times the representative particle size of a first largest fraction | Ratio of the number of particles included in the first largest group to the number of particles whose particle size ranges from 0.5 to 2.0 times the representative particle size of the first largest fraction |
| --- | --- | --- | --- | --- |
| a | 20 | 460 | 680 | 0.68 |
| b | 30 | 403 | 593 | 0.68 |
| c | 50 | 411 | 659 | 0.62 |
| d | 50 | 479 | 703 | 0.68 |
| e | 70 | 591 | 759 | 0.78 |
| f | 70 | 529 | 721 | 0.73 |
| g | 100 | 581 | 703 | 0.83 |
| h | 100 | 603 | 694 | 0.87 |
| i | 150 | 593 | 701 | 0.85 |
| j | 150 | 593 | 726 | 0.82 |
| k | 200 | 631 | 783 | 0.81 |
| l | 200 | 645 | 745 | 0.87 |
| m | 250 | 621 | 731 | 0.85 |
| n | 250 | 623 | 739 | 0.84 |
| o | 250 | 631 | 753 | 0.84 |

Organic particles were prepared by a suspension polymerization of the monomers shown in Table 4.

TABLE 4

| Component | Organic particles (part by weight) |
| --- | --- |
| Bis-GMA | 60 |
| TEGDMA | 40 |
| CQ | 1 |
| DMABE | 1 |
| Refractive index | 1.5182 |

Bis-GMA: 2,2-bis(4-(3-methacryloyloxy-2-hydroxypropoxy)phenyl)propane
TEGDMA: Triethylene glycol dimethacrylate
CQ: dl-camphorquinone
DMABE: Ethyl p-N,N-dimethylaminobenzoate With regard to the organic particles used in Examples, the representative particle size of the first largest fraction, the number of particles included in a group of particles whose particle size ranges from 0.7 to 1.5 times the representative particle size of the first largest fraction (i.e., the number of particles included in the first largest group), the number of particles included in a group of particles whose particle size ranges from 0.5 to 2.0 times the representative particle size of a first largest fraction, and the ratio of the number of particles included in the first largest group to the number of particles whose particle size ranges from 0.5 to 2.0 times the representative particle size of the first largest fraction are shown in Tables 5 and 6.

TABLE 5

| Organic particles | Representative particle size of the first largest fraction [μm] | Number of particles included in the first largest group | Number of particles included in a group of particles whose particle size ranges from 0.5 to 2.0 times the representative particle size of a first largest fraction | Ratio of the number of particles included in the first largest group to the number of particles whose particle size ranges from 0.5 to 2.0 times the representative particle size of the first largest fraction |
|---|---|---|---|---|
| P | 160 | 725 | 845 | 0.86 |
| Q | 900 | 659 | 769 | 0.86 |

TABLE 6

| Organic particles | Representative particle size of the first largest fraction [μm] | Number of particles included in the first largest group | Number of particles included in a group of particles whose particle size ranges from 0.5 to 2.0 times the representative particle size of a first largest fraction | Ratio of the number of particles included in the first largest group to the number of particles whose particle size ranges from 0.5 to 2.0 times the representative particle size of the first largest fraction |
|---|---|---|---|---|
| p | 30 | 403 | 593 | 0.68 |
| q | 200 | 645 | 745 | 0.87 |

Test 1: Filling Property of the Paste.

Dental compositions in the form of paste according to the present invention were filled in a mold having a hole of 4 mm φ×4 mm. The filling property of the dental composition was evaluated based on the following evaluation criteria:

A. excellent filling property: both the extensibility and the formative property are good;

B. suitable filling property: either the extensibility or the formative property is good;

C. practical filling property: either the extensibility or the formative property is inappropriate, sufficient for use; and D. unpractical filling property: both of the extensibility and the formative property are inappropriate and cannot be used.

Test 2: Preservation Stability of the Paste.

Dental compositions in the form of paste according to the present invention were filled in a mold having a hole of 4 mm φ×4 mm and stood for 48 hours. After 48 hours, the preservation stability of the dental composition was evaluated based on the dispersion of the filler in the resin matrix.

A. excellent preservation stability: the fillers disperse homogeneously in the resin matrix;

B. practical preservation stability: the fillers disperse in the resin matrix but partially precipitates, sufficient for use; and C. unpractical preservation stability: the fillers precipitate and separate off the resin matrix cannot be used.

Test 3: Rate of Polymerization Shrinkage.

Dental compositions according the present invention were filled in a clear acrylic mold with a thickness of 5 mm, a wide of 1 cm and a length of 5 cm and each of the top and bottom faces were exposed to light for 3 minutes each for three times using SOLIDILIGHT II (Shofu Inc.) to give cured products. Seven cured products were prepared from one dental composition. The cured products were removed from the mold. The lengths of the cured products were measured with a micrometer and the rate of polymerization shrinkage (%) from the length of the mold (5 cm) was calculated. The average of the rate of polymerization shrinkage was evaluated based on the following evaluation criteria.

AAA. the rate of polymerization shrinkage is less than 0.05%, extremely excellent:

AA. the rate of polymerization shrinkage is more than 0.05% and 0.10% or less, excellent:

A. the rate of polymerization shrinkage is more than 0.10% and 0.15% or less;

B. the rate of polymerization shrinkage is more than 0.20% and 0.30% or less, good:

C. the rate of polymerization shrinkage is from more than 0.30% to 0.40% or less;

D. the rate of polymerization shrinkage is from more than 0.40% to 0.05% or less, practical: and E. the rate of polymerization shrinkage is more than 0.50%, unpractical.

Test 4: Surface Texture of the Cured Product.

Dental compositions of the present invention in the form of paste were filled in the mold and either top or bottom face of the paste was exposed to light for 3 minutes each for three times using SOLIDILIGHT II (Shofu Inc.). The surface texture of the surface opposite to that exposed to light (i.e., presence or absence of sink mark) was evaluated based on the following evaluation criteria:

AA. excellent: the surface is particularly smooth and gloss;

A. good: the surface is smooth and gloss;

B. practical: the surface is either smooth or gloss; and

C. unpractical: the surface is visibly irregular.

The resin matrix was prepared by mixing 60 parts by weight of 2,2-bis(4-(3-methacryloyloxy-2-hydroxypropoxy)phenyl)propane (Bis-GMA), 40 parts by weight of triethylene glycol dimethacrylate (TEGDMA), 1 part by weight of dl-camphorquinone (CQ) and 1 part by weight of ethyl p-N,N-dimethylaminobenzoate (DMABE). The prepared resin matrix was exposed to light for 3 minutes using SOLIDILIGHT II (Shofu Inc.) to obtain cured product. The refractive index of the cured product was 1.5182.

Pastes were prepared by kneading the above obtained resin matrix and the particles (filler) shown in Table 2 in an amount 85% by weight based on the weight of the resin matrix (Table 7).

TABLE 7

|  | Filler shown in Table 2 | Filler content (% by weight) |
|---|---|---|
| Example 1 | A | 85 |
| Example 2 | B | 85 |
| Example 3 | C | 85 |
| Example 4 | D | 85 |
| Example 5 | E | 85 |
| Example 6 | F | 85 |
| Example 7 | G | 85 |
| Example 8 | H | 85 |
| Example 9 | I | 85 |
| Example 10 | J | 85 |
| Example 11 | K | 85 |
| Example 12 | L | 85 |
| Example 13 | M | 85 |
| Example 14 | N | 85 |
| Example 15 | O | 85 |

The above TESTs 1 to 4 were conducted with the dental compositions of the present invention shown in Table 7 (Table 8).

TABLE 8

|  | Filling property to a mold | Preservation stability | Rate of polymerization shrinkage | Surface texture |
|---|---|---|---|---|
| Example 1 | C | C | D | B |
| Example 2 | C | C | D | B |
| Example 3 | C | C | D | B |
| Example 4 | C | C | D | B |
| Example 5 | C | C | B | B |
| Example 6 | C | C | B | B |
| Example 7 | C | B | B | B |
| Example 8 | C | B | B | B |
| Example 9 | C | B | B | B |
| Example 10 | C | C | B | B |
| Example 11 | C | B | B | B |
| Example 12 | C | C | A | B |
| Example 13 | D | B | A | C |
| Example 14 | D | C | A | C |
| Example 15 | D | C | A | C |

As shown in Table 8, the dental compositions of Examples 1 to 12 in the form of paste exhibited filling property enough for the practical use. The dental composition of Examples 7-9, 11, and 13 in the form of paste exhibited preservation stability enough for the practical use.

The cured products of the dental compositions of Examples 5 to 15 provided rate of polymerization shrinkage enough for the practical use. Particularly, the cured products of Examples 12 to 15 were very good that they had a low-rate of polymerization shrinkage. The cured products of Examples 1 to 12 had a surface texture enough for the practical use.

Dental compositions having a practical or good rate of polymerization shrinkage and a practical or good surface texture are preferable because the cured product formed from the dental composition tends to develop less internal stress and be excellent in mechanical strength. When a cured product such as a dental block has a surface texture that does not suit for practical use, the surface of the dental block must be cut and ground so as to make the surface smooth and glossy. Taken together, the results of TESTs showed that the dental compositions of Examples 7-9 and 11 were preferably used for manufacturing dental prostheses and dental blocks.

Pastes were prepared by kneading the above obtained resin matrix and the particles shown in Tables 2 and 3 according to the following formulation

TABLE 9

|  | Filler of Table 2 | Filler of Table 3 | Particle number ratio of the fillers $\alpha$ | Filler amount $\beta$ (% by weight) |
|---|---|---|---|---|
| Example 16 | A | a | 1.0 | 80 |
| Example 17 | A | b | 1.0 | 80 |
| Example 18 | A | c | 1.0 | 80 |
| Example 19 | B | a | 1.0 | 80 |
| Example 20 | B | b | 1.0 | 80 |
| Example 21 | B | c | 1.0 | 80 |
| Example 22 | C | c | 1.0 | 80 |
| Example 23 | C | e | 1.0 | 80 |
| Example 24 | D | a | 1.0 | 80 |
| Example 25 | D | c | 1.0 | 80 |
| Example 26 | E | b | 1.0 | 84 |
| Example 27 | E | e | 1.0 | 84 |
| Example 28 | E | g | 1.0 | 84 |
| Example 29 | F | e | 1.0 | 84 |
| Example 30 | J | b | 1.0 | 84 |
| Example 31 | J | c | 1.0 | 84 |
| Example 32 | J | g | 1.0 | 84 |
| Example 33 | J | i | 1.0 | 84 |
| Example 34 | L | c | 1.0 | 86 |
| Example 35 | L | l | 1.0 | 86 |
| Example 36 | L | n | 1.0 | 86 |
| Example 37 | M | g | 1.0 | 86 |
| Example 38 | M | l | 1.0 | 86 |
| Example 39 | M | n | 1.0 | 86 |
| Example 40 | N | e | 1.0 | 86 |
| Example 41 | N | g | 1.0 | 86 |
| Example 42 | N | m | 1.0 | 86 |
| Example 43 | N | n | 1.0 | 86 |
| Example 44 | B | b | 0.5 | 80 |
| Example 45 | B | b | 0.7 | 80 |
| Example 46 | B | b | 0.9 | 80 |
| Example 47 | B | b | 1.2 | 80 |
| Example 48 | B | b | 1.5 | 80 |
| Example 49 | B | b | 2.0 | 80 |

$\alpha$ The ratio of the number of particles of Table 3 to the number of particles of Table 2 per one unit mass of the mixture.
$\beta$ The amount (% by weight) of the fillers in total based on the dental composition which comprises resin matrix and a mixture of the fillers of Table 2 and Table 3.

The above TESTs 1 to 4 were conducted with the dental compositions shown in Table 9 (Table 10).

TABLE 10

|  | Filling property to a mold | Preservation stability | Rate of polymerization shrinkage | Surface texture |
|---|---|---|---|---|
| Example 16 | A | A | AA | AA |
| Example 17 | A | A | AA | AA |
| Example 18 | B | A | A | B |
| Example 19 | A | A | A | A |
| Example 20 | A | A | AA | AA |
| Example 21 | B | A | A | B |
| Example 22 | A | A | AA | AA |
| Example 23 | B | A | A | B |
| Example 24 | A | A | A | A |
| Example 25 | B | A | A | B |
| Example 26 | A | A | AA | A |
| Example 27 | A | A | AAA | AA |
| Example 28 | B | A | A | B |
| Example 29 | A | A | AA | AA |
| Example 30 | B | A | A | B |
| Example 31 | A | A | AAA | A |
| Example 32 | A | A | AAA | AA |
| Example 33 | B | A | A | B |
| Example 34 | B | A | A | B |
| Example 35 | A | A | AAA | AA |
| Example 36 | B | A | A | B |
| Example 37 | A | A | AA | A |
| Example 38 | A | A | AAA | AA |
| Example 39 | B | A | A | B |
| Example 40 | B | A | A | B |
| Example 41 | A | A | A | A |

TABLE 10-continued

|  | Filling property to a mold | Preservation stability | Rate of polymerization shrinkage | Surface texture |
|---|---|---|---|---|
| Example 42 | A | A | AAA | AA |
| Example 43 | A | A | A | A |
| Example 44 | B | B | B | B |
| Example 45 | B | A | A | A |
| Example 46 | A | A | AA | AA |
| Example 47 | A | A | AA | AA |
| Example 48 | A | A | A | A |
| Example 49 | A | B | A | A |

As shown in Table 10, the dental compositions of Examples 16-43, 46, and 47 in the form of paste exhibited filling property enough for the practical use. Dental compositions having an excellent filling property are preferable that they are suited to repair a cavity of tooth as a repairing agent. Accordingly, the dental compositions of Examples 16-17, 19-20, 22, 24, 26-27, 29, 31-32, 35, 37-38, 41, and 43 were particularly preferred. The dental compositions of Examples 16-43, and 45-48 in the form of paste exhibited preservation stability enough for the practical use.

Dental compositions having an excellent rate of polymerization shrinkage and an excellent surface texture are preferable because the cured product formed from the dental composition tends to develop less internal stress and be excellent in mechanical strength. Accordingly, the dental compositions of Examples 16-17, 19-20, 22, 24, 26-27, 29, 31-32, 35, 37-38, 41-43, and 46-47 had good properties as a dental composition. Further, the dental compositions of Examples 16-17, 19-20, 22, 24, 26-27, 29, 31-32, 35, 37-38, and 41-43 had excellent properties as a dental composition.

The dental composition of Example 20 shown in Table 10 was cured by exposing to light using SOLIDILIGHT II (Shofu Inc.) to give cured dental blocks. One of the dental blocks was ground by means of a CAD/CAM system equipped with a dental router. The other was ground by a dental technician by hand with a dental router. The dental block ground by the CAD/CAM system had glossy uniform surface, as shown in FIG. 1. The ground surface of the dental block was largely occupied by cross sectional surfaces of glass particles, and therefore, the surface was excellent in the mechanical strength. On the other hand, the ground surface of the cured product ground by hand was irregular along with the shape of glass particles in the product as fillers and was not glossy as shown in FIG. 2.

Pastes were prepared by kneading the above obtained resin matrix and the particles shown in Tables 5 and 6 according to the following formulation (Table 11).

TABLE 11

|  | Filler shown in Table 2 | Filler shown in Table 3 | Particle number ratio of fillers [α] | Filler amount [β] (% by weight) |
|---|---|---|---|---|
| Example 50 | P | — | — | 80 |
| Example 51 | P | p | 1.0 | 80 |
| Example 52 | Q | q | 1.0 | 86 |

[α] The ratio of the number of particles of Table 6 to the number of particles of Table 5 per an unit mass of the mixture.
[β] The amount (% by weight) of the filler in total based on the dental composition which comprises resin matrix and a mixture of the filler of Table 5 and Table 6.

The above TESTs 1 to 4 were conducted with the dental compositions shown in Table 11 (Table 12).

TABLE 12

|  | Filling property to a metal mold | Preservation stability | Rate of polymerization shrinkage | Surface texture |
|---|---|---|---|---|
| Example 50 | C | C | D | B |
| Example 51 | A | A | AA | AA |
| Example 52 | A | A | AAA | AA |

As shown in Table 12, the dental composition of Example 50 in the form of paste exhibited filling property enough for the practical use. The cured products of the dental composition of Example 50 had a surface texture enough for the practical use.

The dental compositions of Examples 51 and 52 exhibited an excellent filling property and excellent preservation stability in the form of paste and had a very low-rate of polymerization shrinkage and excellent surface texture in the form of cured material. Dental compositions having an excellent filling property are preferable that they are suited to repair a cavity of tooth as a repairing agent. Accordingly, the dental compositions of Examples 51 and 52 are particularly preferred.

Dental compositions having a low rate of polymerization shrinkage and an excellent surface texture are particularly preferable because the cured product formed from the dental composition tends to develop less internal stress and be excellent in mechanical strength. Taken together, the results of TESTs showed that the dental compositions of Examples 51 and 52 had excellent properties as a dental composition.

In view of the weight of "dental block" or "dental prosthesis" which is formed from the dental composition, the filler included in the dental composition is preferably an organic filler used in the dental field. Dental compositions comprising a resin matrix and organic filler are generally preferable because the cured product formed from said dental composition is easily ground by a dental router to obtain a glossy surface. In addition, the cured composition causes less impact on the edge of the dental router.

What is claimed is:

1. A dental composition consisting essentially of:
   a plurality of particles including a first group of said particles and a second group of said particles, a size of said particles being within a range from 10 μm to 1000 μm;
   a third group of particles each having a particle size less than 1 μm, an average particle size of said third group being within a range from 1 nm to 300 nm; and
   resin matrix,
   wherein said first group consists of a quantity of said particles whose particle size ranges from 0.7 to 1.5 times a first class value of a first largest fraction;
   wherein said first largest fraction is a fraction with a highest frequency in a first frequency distribution table for a quantity of particles with particle sizes ranging from 0.5 to 2.0 times a class value A of a largest fraction with a highest frequency in a frequency distribution table A for a quantity of 1000 particles of said plurality of particles;
   wherein the frequency distribution table A has 32 fractions;
   wherein the first frequency distribution table has fractions calculated based on a square-root choice $\sqrt{n}$, in which n is a quantity of said particles having a particle size ranging from 0.5 to 2.0 times the class value A;
   wherein a ratio of a quantity of said particles included in said first group to a quantity of said particles whose particle size ranges from 0.5 to 2.0 times the first class value is within a range of 0.8 to 1.0 when the first class value is equal to or more than 110 µm;

wherein the ratio of the quantity of said particles included in said first group to the quantity of said particles whose particle size ranges from 0.5 to 2.0 times the first class value is within a range of 0.6 to 1.0 when the class value is less than 110 µm;

wherein said second group consists of said particles whose particle size ranges from 0.7 to 1.5 times a second class value of a second largest fraction;

wherein said second largest fraction is a fraction with a highest frequency in a second frequency distribution table for a quantity of particles with particle sizes ranging from 0.5 to 2.0 times a class value B of a largest fraction with a highest frequency in a frequency distribution table B which is identical to the frequency distribution table A but excludes fractions that contain said particles having particle sizes ranging from 0.7 to 1.5 times the first class value;

wherein the second frequency distribution table has fractions calculated based on a square-root choice √n, in which n is a quantity of said particles having a particle size ranging from 0.5 to 2.0 times the class value B;

wherein a ratio of a quantity of said particles included in the second group to a quantity of said particles whose particle size ranges from 0.5 to 2.0 times the second class value is within a range of 0.8 to 1.0;

wherein the second class value is in a range from 400 µm to less than 700 µm;

wherein a ratio of the first class value to the second class value is within a range between 0.1 and 0.3;

wherein a ratio of the quantity of said particles in said first group to the quantity of said particles in said second group is between 0.7 and 4.0;

wherein a total quantity of said particles in said first group and said particles in said second group is within a range of 80% by weight to 99.5% by weight based on a total weight of the dental composition; and wherein each of said first group of said particles and each of said second group of said particles is a spherical particle formed of organic material, the organic material being selected from a group consisting of methyl (meth)acrylate, ethyl (meth)acrylate, butyl (meth)acrylate, hexyl (meth)acrylate, tetrahydrofurfuryl (meth) acrylate, 2-hydroxyethyl(meth)acrylate, grycidyl (meth)acrylate, lauryl (meth)acrylate, cyclohexyl (meth)acrylate, benzil (meth)acrylate, allyl (meth)acrylate, 2-ethoxyethyl (meth)acrylate, methoxy polyethylene glycol (meth)acrylate, glycerol (meth)acrylate, isobornyl (meth)acrylate, γ-(meth)acryloyloxypropyltrimethoxysilane, γ-(meth)acryloyloxypropyltriethoxysilane, 2-(N,N-dimethylamino)ethyl (meth)acrylate, N-methylol (meth)acrylamide, diacetone (meth)acrylamide, 2,2-bis(4-(meth)acryloyloxyphenyl)propane, 2,2-bis(4-(3-(meth)acryloyloxy-2-hydroxypropoxy) phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentathoxyphenyl)propane, 2,2-bis(4-(meth)acryloyloxydipropooxyphenyl)propane, 2,2-bis(4-(meth)acryloyloxyethoxyphenyl)-2-(4-(meth)acryloyloxydiethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxydipropoxyphenyl)propane, 2,2-bis(4-(meth)acryloyloxyisopropoxyphenyl)propane, 2-hydroxy-3-acryloyloxypropylmethacrylate, hydroxypivalic acid neopentylglycol di(meth)acrylate, ehylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, glycerin di(meth)acrylate, trimethylolpropane tri(meth)acrylate, treimethylolethane tri(meth)acrylate, trimethylolmethane tri(meth) acrylate, pentaerythritol tri(meth) acrylate, pentaerythritol tetra(meth)acrylate, and ditrimethylolporpane tetra (meth) acrylate.

2. The dental composition of claim 1, wherein said first group of said particles and said second group of said particles are dyed particles.

3. The dental composition of claim 1, wherein a total quantity of said particles in said first group and said particles in said second group is within a range from 80% to 95% by weight based on a total weight of the dental composition.

4. A dental composition, obtained by a process comprising a step of:

kneading a material consisting essentially of a plurality of particles including a first group of said particles, a second group of said particles, a third group of said particles each having a particle size less than 1 µm, an average particle size of said third group being within a range from 1 nm to 300 nm, and resin matrix, said particles of said first group of particles and said second group of particles having a particle size within a range from 10 µm to 1000 µm;

wherein said first group consists of said particles whose particle size ranges from 0.7 to 1.5 times a first class value of a first largest fraction;

wherein said first largest fraction is a fraction with a highest frequency in a first frequency distribution table for a quantity of particles with particle sizes ranging from 0.5 to 2.0 times a class value A of a largest fraction with a highest frequency in a frequency distribution table A for a quantity of 1000 particles of said plurality of particles;

wherein the frequency distribution table A has 32 fractions;

wherein the first frequency distribution table has fractions calculated based on a square-root choice √n, in which n is a quantity of said particles having a particle size ranging from 0.5 to 2.0 times the class value A;

wherein said second group consists of said particles whose particle size ranges from 0.7 to 1.5 times a second class value of a second largest fraction;

wherein said second largest fraction is a fraction with a highest frequency in a second frequency distribution table for a quantity of particles with particle sizes ranging from 0.5 to 2.0 times a class value B of a largest fraction with a highest frequency in a frequency distribution table B which is identical to the frequency distribution table A but excludes fractions that contain said particles having particle sizes ranging from 0.7 to 1.5 times the first class value;

wherein the second frequency distribution table has fractions calculated based on a square-root choice √n, in which n is a quantity of said particles having a particle size ranging from 0.5 to 2.0 times the class value B;

wherein a ratio of a quantity of said particles included in said first group to a quantity of said particles whose particle size ranges from 0.5 to 2.0 times the first class value is within a range of 0.8 to 1.0 when the first class value is equal to or more than 110 µm;

wherein the ratio of the quantity of said particles included in said first group to the quantity of said particles whose particle size ranges from 0.5 to 2.0 times the first class value is within a range of 0.6 to 1.0 when the first class value is less than 110 µm;

wherein a ratio of a quantity of said particles included in said second group to a quantity of said particles whose particle size ranges from 0.5 to 2.0 times the second class value is within a range of 0.8 to 1.0;

wherein the second class value is in a range from 400 µm to less than 700 µm;

wherein a ratio of the first class value to the second class value is between 0.1 and 0.3;

wherein a ratio of the quantity of said particles in said first group to the quantity of said particles in said second group is between 0.7 and 4.0;

wherein a total quantity of said particles in said first group and said particles in said second group is within a range of 80% by weight to 99.5% by weight based on a total weight of the dental composition; and wherein each of said first group of said particles and each of said second group of said particles is a spherical particle formed of organic material, the organic material being selected from a group consisting of methyl (meth)acrylate, ethyl (meth)acrylate, butyl (meth)acrylate, hexyl (meth)acrylate, tetrahydrofurfuryl (meth)acrylate, 2-hydroxyethyl(meth)acrylate, grycidyl (meth)acrylate, lauryl (meth)acrylate, cyclohexyl (meth)acrylate, benzil (meth)acrylate, allyl (meth)acrylate, 2-ethoxyethyl (meth)acrylate, methoxy polyethylene glycol (meth)acrylate, glycerol (meth)acrylate, isobornyl (meth)acrylate, γ-(meth)acryloyloxypropyltrimethoxysilane, γ-(meth)acryloyloxypropyltriethoxysilane, 2-(N,N-dimethylamino)ethyl (meth)acrylate, N-methylol (meth)acrylamide, diacetone (meth)acryl amide, 2,2-bis(4-(meth)acryloyloxyphenyl)propane, 2,2-bis(4-(3-(meth)acryloyloxy-2-hydroxypropoxy)phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentathoxyphenyl)propane, 2,2-bis(4-(meth)acryloyloxydipropooxyphenyl)propane, 2,2-bis(4-(meth)acryloyloxyethoxyphenyl)-2-(4-(meth)acryloyloxydiethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxydipropoxyphenyl)propane, 2,2-bis(4-(meth)acryloyloxyisopropoxyphenyl)propane, 2-hydroxy-3-acryloyloxypropylmethacrylate, hydroxypivalic acid neopentylglycol di(meth)acrylate, ehylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, glycerin di(meth)acrylate, trimethylolpropane tri(meth)acrylate, treimethylolethane tri(meth)acrylate, trimethylolmethane tri(meth) acrylate, pentaerythritol tri(meth) acrylate, pentaerythritol tetra(meth)acrylate, and ditrimethylolporpane tetra (meth) acrylate.

5. The dental composition of claim 4, wherein said first group of said particles and said second group of said particles are dyed particles.

6. The dental composition of claim 4, wherein a total quantity of said particles in said first group and said particles in said second group is within a range from 80% to 95% by weight based on a total weight of the dental composition.

7. A dental block or a dental prosthesis, which is formed from the dental composition of claim 1.

8. A dental composition consisting essentially of:

a plurality of particles consisting of a first group of said particles and a second group of said particles, a size of said particles being within a range from 10 µm to 1000 µm; and resin matrix, wherein said first group consists of a quantity of said particles whose particle size ranges from 0.7 to 1.5 times a first class value of a first largest fraction;

wherein said first largest fraction is a fraction with a highest frequency in a first frequency distribution table for a quantity of particles with particle sizes ranging from 0.5 to 2.0 times a class value A of a largest fraction with a highest frequency in a frequency distribution table A for a quantity of 1000 particles of said plurality of particles;

wherein the frequency distribution table A has 32 fractions;

wherein the first frequency distribution table has fractions calculated based on a square-root choice √n, in which n is a quantity of said particles having a particle size ranging from 0.5 to 2.0 times the class value A;

wherein a ratio of a quantity of said particles included in said first group to a quantity of said particles whose particle size ranges from 0.5 to 2.0 times the first class value is within a range of 0.8 to 1.0 when the first class value is equal to or more than 110 µm;

wherein the ratio of the quantity of said particles included in said first group to the quantity of said particles whose particle size ranges from 0.5 to 2.0 times the first class value is within a range of 0.6 to 1.0 when the class value is less than 110 µm;

wherein said second group consists of said particles whose particle size ranges from 0.7 to 1.5 times a second class value of a second largest fraction;

wherein said second largest fraction is a fraction with a highest frequency in a second frequency distribution table for a quantity of particles with particle sizes ranging from 0.5 to 2.0 times a class value B of a largest fraction with a highest frequency in a frequency distribution table B which is identical to the frequency distribution table A but excludes fractions that contain said particles having particle sizes ranging from 0.7 to 1.5 times the first class value;

wherein the second frequency distribution table has fractions calculated based on a square-root choice √n, in which n is a quantity of said particles having a particle size ranging from 0.5 to 2.0 times the class value B;

wherein a ratio of a quantity of said particles included in the second group to a quantity of said particles whose particle size ranges from 0.5 to 2.0 times the second class value is within a range of 0.8 to 1.0;

wherein the second class value is in a range from 400 µm to less than 700 µm;

wherein a ratio of the first class value to the second class value is within a range between 0.1 and 0.3;

wherein a ratio of the quantity of said particles in said first group to the quantity of said particles in said second group is between 0.7 and 4.0;

wherein a total quantity of said particles in said first group and said particles in said second group is within a range from 80.0% to 99.5% by weight based on a total weight of the dental composition; and wherein each of said first group of said particles and each of said second group of said particles is a spherical particle formed of organic material, the the organic material being selected from a group consisting of methyl (meth)acrylate, ethyl (meth)acrylate, butyl (meth)acrylate, hexyl (meth)acrylate, tetrahydrofurfuryl (meth)acrylate, 2-hydroxyethyl(meth)acrylate, grycidyl (meth)acrylate, lauryl (meth)acrylate, cyclohexyl (meth)acrylate, benzil (meth)acrylate, allyl (meth)acrylate, 2-ethoxyethyl (meth)acrylate, methoxy polyethylene glycol (meth)acrylate, glycerol (meth)acrylate, isobornyl (meth)acrylate, γ-(meth)acryloyloxypropyltrimethoxysilane, γ-(meth)acryloyloxypropyltriethoxysilane, 2-(N,N-dimethylamino)ethyl (meth)acrylate, N-methylol (meth)acrylamide, diacetone (meth)acryl amide, 2,2-bis(4-(meth)acryloyloxyphenyl)propane, 2,2-bis(4-(3-(meth)acryloyloxy-2-hydroxypropoxy) phenyl)propane, 2,2-bis(4-(meth)acryloyloxyethoxyphenyl)propane, 2,2-bis(4-(meth)acryloyloxydiethoxyphenyl)propane, 2,2-bis(4-(meth) acryloyloxytetraethoxyphenyl)propane, 2,2-bis(4-(meth)acryloyloxypentathoxyphenyl)propane, 2,2-bis (4-(meth)acryloyloxydipropooxyphenyl)propane, 2,2-bis(4-(meth)acryloyloxyethoxyphenyl)-2-(4-(meth) acryloyloxydiethoxyphenyl)propane, 2-(4-(meth) acryloyloxydiethoxyphenyl)-2-(4-(meth) acryloyloxytriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxydipropoxyphenyl)propane, 2,2-bis(4-(meth)acryloyloxyisopropoxyphenyl)propane, 2-hydroxy-3-acryloyloxypropylmethacrylate, hydroxypivalic acid neopentylglycol di(meth)acrylate, ehylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, glycerin di(meth)acrylate, trimethylolpropane tri(meth)acrylate, treimethylolethane tri(meth)acrylate, trimethylolmethane tri(meth) acrylate, pentaerythritol tri(meth) acrylate, pentaerythritol tetra(meth)acrylate, and ditrimethylolporpane tetra (meth) acrylate.

9. The dental composition of claim 8, wherein said first group of said particles and said second group of said particles are dyed particles.

10. The dental composition of claim 8, wherein a total quantity of said particles in said first group and said particles in said second group is within a range from 80% to 95% by weight based on a total weight of the dental composition.

* * * * *